(12) United States Patent
Cai et al.

(10) Patent No.: US 11,866,703 B2
(45) Date of Patent: Jan. 9, 2024

(54) **METHOD FOR KNOCKING OUT N-MYRISTOYLTRANSFERASE (NMT) GENE FROM *EIMERIA TENELLA***

(71) Applicant: LANZHOU VETERINARY RESEARCH INST., CHINESE ACADEMY OF AGRICULTURAL SCIENCES, Lanzhou (CN)

(72) Inventors: Jianping Cai, Lanzhou (CN); Zigang Qu, Lanzhou (CN); Xiao Xu, Lanzhou (CN); Jing Wang, Lanzhou (CN); Zhenxing Gong, Lanzhou (CN); Heng Wang, Lanzhou (CN); Xueyang He, Lanzhou (CN); Wenqing Wang, Lanzhou (CN)

(73) Assignee: LANZHOU VETERINARY RESEARCH INSTITUTE, CHINESE ACADEMY OF AGRICULTURAL SCIENCES, Lanzhou (CN)

(*) Notice: Subject to any disclaimer, the term of this patent is extended or adjusted under 35 U.S.C. 154(b) by 204 days.

(21) Appl. No.: 17/133,300

(22) Filed: Dec. 23, 2020

(65) Prior Publication Data
US 2021/0198670 A1 Jul. 1, 2021

(30) Foreign Application Priority Data
Dec. 26, 2019 (CN) .......................... 201911365073.X

(51) Int. Cl.
*C12N 15/113* (2010.01)
*C12N 9/22* (2006.01)
*C12N 15/79* (2006.01)
*C12N 15/10* (2006.01)

(52) U.S. Cl.
CPC .............. *C12N 15/113* (2013.01); *C12N 9/22* (2013.01); *C12N 15/1031* (2013.01); *C12N 15/79* (2013.01); *C12N 2310/20* (2017.05)

(58) Field of Classification Search
CPC .... C12N 15/113; C12N 9/22; C12N 15/1031; C12N 15/79; C12N 2310/20
See application file for complete search history.

(56) References Cited

PUBLICATIONS

Shen et al., "Efficient Gene Disruption in Diverse Strains of Toxoplasma gondii Using CRISPR/CAS9," mBio 5,3: e01114-14 (2014), (14 pages).

*Primary Examiner* — Nancy J Leith
*Assistant Examiner* — Kyle Thomas Rega
(74) *Attorney, Agent, or Firm* — MH2 TECHNOLOGY LAW GROUP, LLP

(57) ABSTRACT

The present disclosure provides a method for knocking out an N-myristoyltransferase (NMT) gene from *Eimeria tenella*, and belongs to the technical field of microorganisms. The method includes: mixing sporozoites of *Eimeria tenella* with a pCRISPR::EtNMT plasmid and a pEtNMT:: DHFR plasmid, and subjecting a resulting mixture to electrotransformation to obtain NMT gene-knockout *Eimeria tenella*. The method provided by the present disclosure can successfully knock out the NMT gene from *Eimeria tenella*, which lays a foundation for studying the function of the *Eimeria tenella* gene and developing a vaccine therefor.

10 Claims, 3 Drawing Sheets
Specification includes a Sequence Listing.

SEQUENCE LISTING

<160> NUMBER OF SEQ ID NOS: 24

<210> SEQ ID NO 1
<211> LENGTH: 40
<212> TYPE: DNA
<213> ORGANISM: Artificial Sequence
<220> FEATURE:
<223> OTHER INFORMATION: CRISPR-EtNMT-F(GOI-gRNA-Fw)

<400> SEQUENCE: 1
gctgtgtgtc ccagaacagg gttttagagc tagaaatagc                              40

<210> SEQ ID NO 2
<211> LENGTH: 20
<212> TYPE: DNA
<213> ORGANISM: Artificial Sequence
<220> FEATURE:
<223> OTHER INFORMATION: CRISPR-R(GOI-gRNA-Rv)

<400> SEQUENCE: 2
aacttgacat ccccatttac                                                    20

<210> SEQ ID NO 3
<211> LENGTH: 29
<212> TYPE: DNA
<213> ORGANISM: Artificial Sequence
<220> FEATURE:
<223> OTHER INFORMATION: PCR1-F

<400> SEQUENCE: 3
gatcggatcg gacttgttcg gggctcttt                                          29

<210> SEQ ID NO 4
<211> LENGTH: 28
<212> TYPE: DNA
<213> ORGANISM: Artificial Sequence
<220> FEATURE:
<223> OTHER INFORMATION: PCR1-R

<400> SEQUENCE: 4
gctgcgggcc attgcggtgt cgtggatt                                           28

<210> SEQ ID NO 5
<211> LENGTH: 31
<212> TYPE: DNA
<213> ORGANISM: Artificial Sequence
<220> FEATURE:
<223> OTHER INFORMATION: PCR2-F

<400> SEQUENCE: 5
atgtgcgtgt atccactcgt gaatgcgtta t                                       31

<210> SEQ ID NO 6
<211> LENGTH: 30
<212> TYPE: DNA
<213> ORGANISM: Artificial Sequence
<220> FEATURE:
<223> OTHER INFORMATION: PCR2-R

<400> SEQUENCE: 6
acaagatgcg aagcaaaccc taggccgtaa                                         30

<210> SEQ ID NO 7
<211> LENGTH: 29
<212> TYPE: DNA
<213> ORGANISM: Artificial Sequence
<220> FEATURE:
<223> OTHER INFORMATION: PCR3-F

<400> SEQUENCE: 7
aatttctcat tggttagttc caagagaag                                          29

<210> SEQ ID NO 8
<211> LENGTH: 27
<212> TYPE: DNA
<213> ORGANISM: Artificial Sequence
<220> FEATURE:
<223> OTHER INFORMATION: PCR3-R

<400> SEQUENCE: 8
cccgtcgcca actccaaact tcaattc                                            27

<210> SEQ ID NO 9
<211> LENGTH: 29
<212> TYPE: DNA

```
<213> ORGANISM: Artificial Sequence
<220> FEATURE:
<223> OTHER INFORMATION: EtNMT-F

<400> SEQUENCE: 9
atgcctgcag actgcaaaga aaatgcagc                                  29

<210> SEQ ID NO 10
<211> LENGTH: 32
<212> TYPE: DNA
<213> ORGANISM: Artificial Sequence
<220> FEATURE:
<223> OTHER INFORMATION: EtNMT-R

<400> SEQUENCE: 10
ttagaggagc gccaagccaa tatctttgtg ca                              32

<210> SEQ ID NO 11
<211> LENGTH: 20
<212> TYPE: DNA
<213> ORGANISM: Artificial Sequence
<220> FEATURE:
<223> OTHER INFORMATION: target sequence

<400> SEQUENCE: 11
cctgttctgg gacacacagc                                            20

<210> SEQ ID NO 12
<211> LENGTH: 45
<212> TYPE: DNA
<213> ORGANISM: Artificial Sequence
<220> FEATURE:
<223> OTHER INFORMATION: EtNMT5'UTR-F

<400> SEQUENCE: 12
ctagcgttta aacttaagct tcctaaaccc taatgctaaa ccctt                45

<210> SEQ ID NO 13
<211> LENGTH: 31
<212> TYPE: DNA
<213> ORGANISM: Artificial Sequence
<220> FEATURE:
<223> OTHER INFORMATION: EtNMT5'UTR-R

<400> SEQUENCE: 13
gaactacgcg tttgcagtct gcaggcattt t                               31

<210> SEQ ID NO 14
<211> LENGTH: 32
<212> TYPE: DNA
<213> ORGANISM: Artificial Sequence
<220> FEATURE:
<223> OTHER INFORMATION: DHFR-F

<400> SEQUENCE: 14
agactgcaaa cgcgtagttc ctgtgtgtca tt                              32

<210> SEQ ID NO 15
<211> LENGTH: 31
<212> TYPE: DNA
<213> ORGANISM: Artificial Sequence
<220> FEATURE:
<223> OTHER INFORMATION: DHFR-R

<400> SEQUENCE: 15
agcaccaagc ggaattccat cctgcaagtg c                               31
```

<210> SEQ ID NO 16
<211> LENGTH: 31
<212> TYPE: DNA
<213> ORGANISM: Artificial Sequence
<220> FEATURE:
<223> OTHER INFORMATION: EtNMT3'UTR-F

<400> SEQUENCE: 16
atggaattcc gcttggtgct cctctaaacc c                               31

<210> SEQ ID NO 17
<211> LENGTH: 39
<212> TYPE: DNA
<213> ORGANISM: Artificial Sequence
<220> FEATURE:
<223> OTHER INFORMATION: EtNMT3'UTR-R

<400> SEQUENCE: 17
ccacactgga ctagtggatc cagacaccgc ggccgccag                       39

<210> SEQ ID NO 18
<211> LENGTH: 1088
<212> TYPE: DNA
<213> ORGANISM: Artificial Sequence
<220> FEATURE:
<223> OTHER INFORMATION: the upstream 5' UTR of the EtNMT gene

<400> SEQUENCE: 18
cctaaaccct aatgctaaac ccttatgtta gcaaacggat ggcatcttta taggataaat      60
atgaaatgca tctgaagttg tttggttttc catttcgcac tttgagtgca aaccctaacc     120
cgtaaaccct aaaccctaaa ccctaaaccc cgaaccctaa accctagcct cctagcccct     180
gtaacagctc tgcgtgtgtt tccgaattca ttctttggca cttctttgat tttgcaattc     240
aaatcattta aatttcaat ttatttcaaa tatcttttat tttatttatt ttaaaagaag      300
ttaaaacccc gctgcggccg ctggctgccg actttggcga acttgaattt caagtgtctg     360
cacgagttga actcagaact tgaacgaaga ggggaaactg cgcatttctg gggctaaaaa     420
ggccgaaaga gacaaaaata aatgaataaa ttgaataaaa gtgcagataa atggagaatt     480
cgaggaagat attcacaaaa tcgagatctt ttcctcggag tttcttcgga tgaggcgttg     540
ctgtttccaa aacgaacaca gcaactcgcg ggcactgcgg agccgattcg cgccaaaat     600 taacgctttt tagcgtcatc tgcgtcaaat tgaacggcga aaccgaatta attacaaaaa     660
ctaaattaat ttgcgccttt aagtgttaaa aacgggccaa gaggcgcaaa aagaggggag     720
cagccgtccc tgtgctccga cagccccagc tgtacagaca gcatgcggcg ctggcagtgc     780
gtgtgccggt ttaaaattaa attaaattat ttattttaat aaatttgata aatttaattt     840
gtggattctt tgttttcacc cgagcttcgc gcggaaccac ctccaacccc gcggccccg     900 ctgtctttga tcggatcgga cttgttcggg gctcttttc tcttcttttt ctctcctttt     960
gaattcttct tttccaaaat taatttttatt ttactttaag aacttcaaac tctccgggac   1020
gccccttgtt gctgcttttc tcccgaggcc acggaccccc cagcgccaaa atgcctgcag   1080
actgcaaa                                                            1088

<210> SEQ ID NO 19
<211> LENGTH: 1348
<212> TYPE: DNA
<213> ORGANISM: Artificial Sequence
<220> FEATURE:

<223> OTHER INFORMATION: ORF of the EtNMT gene

<400> SEQUENCE: 19

| | |
|---|---|
| atgcctgcag actgcaaaga aaatgcagca gcagcagacg cagcagcaga tccgcagcag | 60 |
| cagcagcagc aacagcaagc aacagcagca gcagcagcag caaaaaaccc agacagctcg | 120 |
| cccaatgccg gaggggatgc cctcagcggc agctttgact cgagccatga gaggattgtc | 180 |
| tgtggccccc cacctgttct gggacacaca gccagtggtg aaggcagcgg agcgggcggc | 240 |
| gctggcccca caggatgagg gccctattga cgctccgaaa acagtagatg atgttagaaa | 300 |
| ggagccttac aatttgccaa gtggttttat ttggtctgaa tgttcggtgg aagacccgca | 360 |
| ggccttggac gaggtgtact ggctgctgag cgaacactac gtggaagacg aagacaattt | 420 |
| gtttcgtttt aattacagcc gggagttttt gttttgggct ttgactcccc cgggggcctt | 480 |
| tagggagtgg attgtgggcg tgcgcgtagc agcaaacaac aaacttgtgg ggctaattac | 540 |
| ggcgagccct gctgcagtga gctgcagcag caaaacgctg cagctggcgg aggtgaattt | 600 |
| tctgtgtgtg cacaagaagc tgcgaagcaa aagactggcc cctgtgctta tcaaggaaat | 660 |
| cactcggcgg gtaaatctca agggcatttg gcaggccgtc tatacagcag gagttgtgct | 720 |
| gccgacgcca gtggcggagt gccgttattg cacagatctt taaatcccaa aaagttaat | 780 |
| tgaagttgga tttagcggac ttggaaaaag aatgacaatt agccggagta ttaagcttta | 840 |
| tagggtggcg gagtcgccgg cgatcgaagg gctgagggaa atgaaggccg agacgtttc | 900 |
| gaaagttcaa agttgttga tgaattattt ggaacagttc aaacttcacc cagtgttttc | 960 |
| ggaggaagaa atttctcatt ggttagttcc aagagaagga gttgttcatg tttatgttcg | 1020 |
| ggaagaagaa ggagaagtga cggatttaat ttcttttac gaattgcctt cttctgtaat | 1080 |
| tggcacagaa aaacacaaag aagtcaaagc tgcttattct ttttacaacg tggccacttc | 1140 |
| ggtgccgctg aaagaactta tgcaagacgc cctttgcctc gccaaacaaa aagacttcga | 1200 |
| cgtatttaac gcgttggatg taatggaaaa taaaaacctt cgtggaggaat tgaagtttgg | 1260 |
| agttggcgac gggtttctgc ggtattacct ttacaactgg cgctgctctc cgttgctgca | 1320 |
| caaagatatt ggcttggtgc tcctctaa | 1348 |

<210> SEQ ID NO 20
<211> LENGTH: 721
<212> TYPE: DNA
<213> ORGANISM: Artificial Sequence
<220> FEATURE:
<223> OTHER INFORMATION: plasmid sequence fragment

<400> SEQUENCE: 20

| | |
|---|---|
| gagcgcagcg agtcagtgag cgaggaagcg gaagagcgcc caatacgcaa accgcctctc | 60 |
| cccgcgcgtt ggccgattca ttaatgcagc tggcacgaca ggtttcccga ctggaaagcg | 120 |
| ggcagtgagc gcaacgcaat taatgtgagt tagctcactc attaggcacc ccaggcttta | 180 |
| cactttatgc ttccggctcg tatgttgtgt ggaattgtga gcggataaca atttcacaca | 240 |
| ggaaacagct atgaccatga ttacgccaag ctcgaaatta accctcacta agggaacaa | 300 |
| aagctggagc tcaaaaaagc accgactcgg tgccactttt caagttgata acggactagc | 360 |
| cttattttaa cttgctattt ctagctctaa aaccctgttc tgggacacac agcaacttga | 420 |
| catccccatt taccagaagg caaacacccc cttcggggac gaggtgaccc tgcgcgacag | 480 |
| aaagcccctt cgaagagcgc acagggagga agcaggcctc tgcaggtcgc catttgaaaa | 540 |
| tctgacagaa ctgatggaaa tatgattctt gtcagagaag acattcgaga gttcgaaggt | 600 |

```
ttccccctttg gctctacata tcccagtgtc tcgcgttctg caggaggcgc gtcaggccta    660
ggatgcaata ttggcgccca attcacagtg cagcggcgca gccgtcgcaa cacttcgcag    720
c                                                                    721
```

<210> SEQ ID NO 21
<211> LENGTH: 1030
<212> TYPE: DNA
<213> ORGANISM: Artificial Sequence
<220> FEATURE:
<223> OTHER INFORMATION: nucleotide sequence of downstream 3' UTR of the EtNMT gene

<400> SEQUENCE: 21

```
gcttggtgct cctctaaacc ctaaaatagg gtttagggtt tacggcctag ggtttgcttc     60
gcatcttgtc gccgcgctgc tgaagcagca gcgctgctgc agcagcagcg ctgctgcaca    120
tctgcagcag aagcaaggct gctgctgcgg cagcaaaagc agcagcaaca gcagcaaagc    180
agcagctgca gcagcaacag cgacgaagca gcagctgcag cagcagcagc tgcagcagca    240
acagcagcag cacaaagcag ctgcagcacc gcagaacagc ggaggcgcct tgctgcagc    300 agcaacaagg actggcgtgt ctatttgttt actactctta ttatcattta tttattttat    360
tttatttatt tatttatttg tttagattta ttgtctcagt tttgcgtcca caaacagaaa    420
tccacatttc ctggagtcga gaggttgcag cagcagcagc agcgctatct gctgctgctg    480
ttgctgctgc aactgctgca ggtgctgctg ctgcagcatg aactcagttg cagctaaaac    540
gcagctgcag ctgcaaaaaa gaattgggga acaaaaaaca aaagagcagc caagccccta    600
aaccctaaac cctaaaccct ccttattccg agaaaaagga gattcgaagg gagctgcttg    660
ctgcagcgca tctgatgcag caactactgc agcaaatact gcagctcgtg cagcaaatgc    720
tgcagcaagt gctgcagcaa gtgcaagttc tgcagcaagt gctgcagcaa gtgccagtgc    780
tacagcgagt gctgcagcaa gtgctgcagc aagtgctgca gcaagtgcca gtgctacagc    840
gagtgctgca gcaagtgctg cagcaagtgc tgcagcaagt gctgcagcaa gtgccagtgc    900
tgcagcaagt gctgcagcaa gtgctgcagc aagtgctgca gcaagtactg cagcaagtgc    960
tgcagcagca cttgctgcag cgtcagaggg cgaagaggat ggcgctgagt tcctggcggc   1020
cgcggtgtct                                                         1030
```

<210> SEQ ID NO 22
<211> LENGTH: 36
<212> TYPE: DNA
<213> ORGANISM: Artificial Sequence
<220> FEATURE:
<223> OTHER INFORMATION: DNA fragment containing the target sequence for knockin

<400> SEQUENCE: 22

```
agatctgtgg cgtctcgatt gtgagagctg gcgagt                               36
```

<210> SEQ ID NO 23
<211> LENGTH: 36
<212> TYPE: DNA
<213> ORGANISM: Artificial Sequence
<220> FEATURE:
<223> OTHER INFORMATION: DNA fragment containing the target sequence for knockin

<400> SEQUENCE: 23

```
tctagacacc gcagagctaa cactctcgac cgctca                               36
```

```
<210> SEQ ID NO 24
<211> LENGTH: 20
<212> TYPE: RNA
<213> ORGANISM: Artificial Sequence
<220> FEATURE:
<223> OTHER INFORMATION: gRNA for knockin

<400> SEQUENCE: 24
ggcgucucga uugugagagc                                              20
```

METHOD FOR KNOCKING OUT N-MYRISTOYLTRANSFERASE (NMT) GENE FROM *EIMERIA TENELLA*

CROSS-REFERENCE TO RELATED APPLICATIONS

This application claims the priority of Chinese Patent Application No. 201911365073.X, filed on Dec. 26, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on 8 Oct. 2023 is named REPLACEMENT SEQUENCE LISTING 10-08-2023 and is 10,364 bytes in size.

TECHNICAL FIELD

The present disclosure belongs to the technical field of microorganisms, and particularly relates to a method for knocking out an N-myristoyltransferase (NMT) gene from *Eimeria tenella*.

BACKGROUND

*Eimeria tenella* is one of the most important pathogens in livestock breeding, which can cause significant economic losses in breeding industries of poultry, rabbit, pig, cattle, sheep, and the like. According to statistics, the global coccidiosis-caused loss in the chicken industry reaches more than 5 billion US dollars every year. The economic loss due to chicken coccidiosis in China is as high as 6 to 7 billion yuan, and the expenditure on drugs alone is more than 1.2 billion. In intensive breeding, anticoccidial drugs are used to prevent and control coccidiosis, which greatly reduces economic losses and promotes the healthy development of poultry industry. However, coccidiosis shows strong resistance to commercial anticoccidial drugs currently in use over time. The prevention and control of coccidiosis still requires novel safe and efficient anticoccidial drugs, and it is urgent to discover new drug targets and novel efficient drugs. The development of novel drugs is based on in-depth knowledge of the biochemical metabolic pathways and key virulence factors of *Eimeria tenella* and of the biology and effectiveness of drug targets.

N-terminal myristoylation is a fatty acylation modification coupled with protein translation, which is an irreversible modification where myristic acid is covalently linked to the N-terminal glycine residue of a nascent peptide chain via an amide bond under the catalysis of NMT. Myristoylation is an important intracellular process, and the substrate protein myristoylation has multiple effects, which can affect the protein-protein interaction, enhance interaction of protein with organelles or plasma membrane, change the protein stability, regulate the enzyme activity, and so on.

A variety of myristoylated proteins are involved in regulating the signaling pathways of cell proliferation and growth. Felsted et al. first proposed use of myristoylation as a chemotherapeutic target for cancer. In addition, NMT can be used as an effective drug target for fungi, viruses, and parasitic protozoa that infect humans. Studies have shown that NMT plays a key role in the survival of *Saccharomyces cerevisiae*, *Cryptococcus neoformans*, *Leishmania major*, *Trypanosoma brucei*, and the like in a host and can be used as a drug target for biological research.

NMT plays an important role in parasites, but there is no method for knocking out an NMT gene from *Eimeria tenella* in the prior art.

SUMMARY

In view of this, the present disclosure is intended to provide a method for knocking out an NMT gene from *Eimeria tenella*. The method provided by the present disclosure can successfully knock out the NMT gene from *Eimeria tenella*, which lays a foundation for studying the function of the *Eimeria tenella* gene and developing a vaccine therefor.

To achieve the above purpose, the present disclosure provides the following technical solutions. The present disclosure provides a method for knocking out an N-myristoyltransferase (NMT) gene from *Eimeria tenella*, including: mixing sporozoites of *Eimeria tenella* with a pCRISPR::EtNMT plasmid and a pEtNMT::DHFR plasmid, and subjecting a resulting mixture to electrotransformation to obtain NMT gene-knockout *Eimeria tenella*.

Preferably, the sporozoites of *Eimeria tenella* are mixed with the pCRISPR::EtNMT plasmid and the pEtNMT::DHFR plasmid at a number-mass-mass ratio of $(0.5\text{-}1.5 \times 10^7)$ sporozoites:$(3\text{-}8)$ μg:$(0.5\text{-}1.5)$ μg.

Preferably, a construction method of the pCRISPR::EtNMT plasmid includes: with a pSAG1::Cas9-U6::sgUPRT plasmid as a template, conducting amplification using a CRISPR-EtNMT-F primer and a CRISPR-R primer to obtain an amplification product; subjecting the amplification product to Kinase, Ligase, and Dpn1 (KLD) reaction to obtain a reaction product; and transforming the reaction product into competent cells, and extracting a resulting plasmid to obtain the pCRISPR::EtNMT plasmid;
  the CRISPR-EtNMT-F primer has a nucleotide sequence shown in SEQ ID NO: 1; and
  the CRISPR-R primer has a nucleotide sequence shown in SEQ ID NO: 2.

Preferably, every 28.5 μl of a system used for the amplification includes: Q5 hot start high-Fidelity 2× Master Mix: 12.5 μl; CRISPR-EtNMT-F primer: 1.25 μl; CRISPR-R primer: 1.25 μl; pSAG1::Cas9-U6::sgUPRT plasmid: 1 μl; and Nuclease-free water: 12.5 μl.

Preferably, a procedure used for the amplification includes: 98° C. for 30 s, 98° C. for 10 s, 55° C. for 30 s, 72° C. for 2 min, 35 cycles; and 72° C. for 2 min.

Preferably, every 10 μl of a system for the KLD reaction includes: amplification product: 1 μl; 2× KLD reaction buffer: 5 μl; 10× KLD enzyme Mix: 1 μl; and Nuclease-free water: 3 μl; and
  the KLD reaction is conducted at 25° C. to 30° C. for 5 min.

Preferably, a construction method of the pEtNMT::DHFR plasmid includes: ligating upstream 5'UTR of an EtNMT gene, DHFR-TS*, and downstream 3'UTR of the EtNMT gene into a pcDNA3.1 (+) vector to obtain a ligated vector; transforming the ligated vector into competent cells; and extracting a resulting plasmid to obtain the pEtNMT::DHFR plasmid.

Preferably, every 10 μl of a system for the ligation includes: 5× In-fusion enzyme premixture: 2 μl; DHFR-TS* gene: 1 μl; upstream 5'UTR of EtNMT gene: 1 μl; downstream 3'UTR of EtNMT gene: 4 μl; and pcDNA3.1 (+) vector: 2 μl; and the ligation is conducted first at 37° C. for 15 min and then at 50° C. for 15 min.

Preferably, after the electrotransformation, the method further includes:
  inoculating an obtained electrotransformation product into MDBK cells for cultivation, adding pyrimethamine at 6 h, and collecting host cells at 24 h;
  lysing and digesting the host cells to obtain cells with sporozoites, attacking chicks using the cells with sporozoites, and collecting feces to obtain oocysts;
  cultivating the oocysts into adult *Eimeria tenella*, and extracting genomic DNA (gDNA) of the adult *Eimeria tenella*; and with the gDNA as a template, conducting amplification using a PCR1 primer pair, a PCR2 primer pair, and a PCR3 primer pair, separately, where, when fragments can be obtained from both the amplification using the PCR1 primer pair and the amplification using the PCR2 primer pair, but no fragments can be obtained from the amplification using the PCR3 primer pair, the *Eimeria tenella* is NMT gene-knockout *Eimeria tenella*.

Preferably, the PCR1 primer pair includes PCR1-F and PCR1-R, the PCR1-F has a nucleotide sequence shown in SEQ ID NO: 3, and the PCR1-R has a nucleotide sequence shown in SEQ ID NO: 4;
  the PCR2 primer pair includes PCR2-F and PCR2-R, the PCR2-F has a nucleotide sequence shown in SEQ ID NO: 5, and the PCR2-R has a nucleotide sequence shown in SEQ ID NO: 6; and
  the PCR3 primer pair includes PCR3-F and PCR3-R, the PCR3-F has a nucleotide sequence shown in SEQ ID NO: 7, and the PCR3-R has a nucleotide sequence shown in SEQ ID NO: 8.

The present disclosure provides a method for knocking out an NMT gene from *Eimeria tenella*, including: mixing sporozoites of *Eimeria tenella* with a pCRISPR::EtNMT plasmid and a pEtNMT::DHFR plasmid, and subjecting a resulting mixture to electrotransformation to obtain NMT gene-knockout *Eimeria tenella*. The method provided by the present disclosure can successfully knock out the NMT gene from *Eimeria tenella*, which lays a foundation for studying the function of the *Eimeria tenella* gene and developing a vaccine therefor.

The mechanism of knocking out the NMT gene from *Eimeria tenella* in the present disclosure is as follows: a single-stranded gRNA with the guiding function (Guide RNA) is used to guide the nuclease Cas9 protein to cleave a double-stranded DNA at a target site paired with the gRNA, causing DNA double-strand break (DSB); and then the non-homologous repair mechanism (NHEJ) or the homologous recombination mechanism (HR) in an organism is used to repair the DNA, leading to gene frameshift mutation, substitution or deletion and thus resulting in loss of gene function.

DETAILED DESCRIPTION

Figure 1:
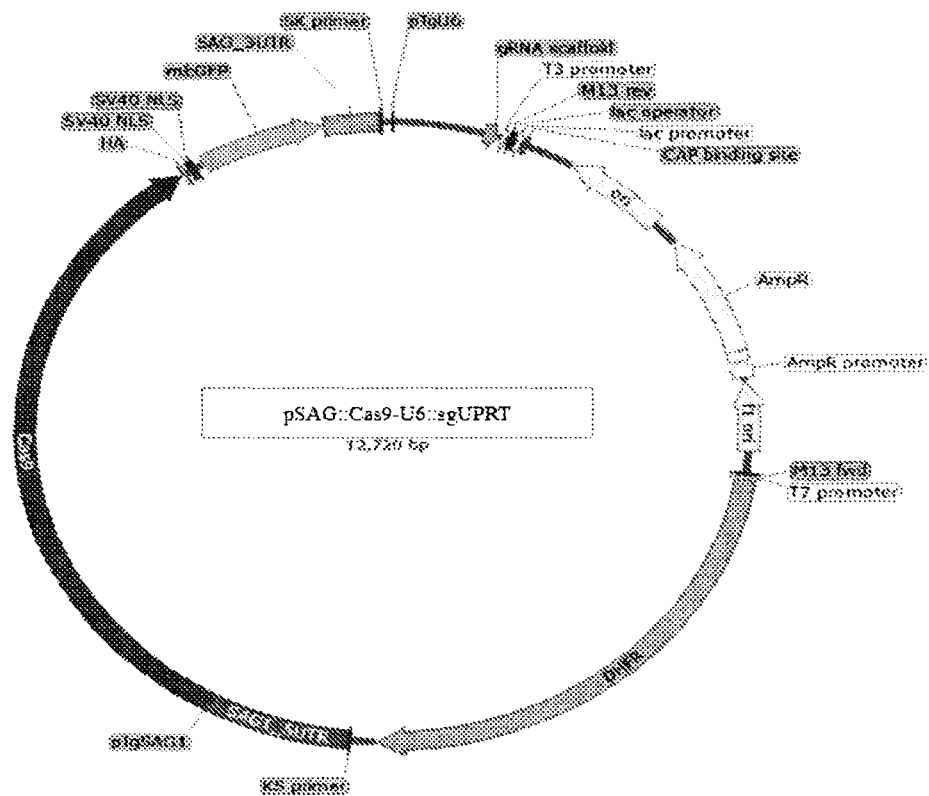
FIG. 1 is a map of the sequence pattern of pSAG::Cas9-U6::UPRT.
Figure 2:
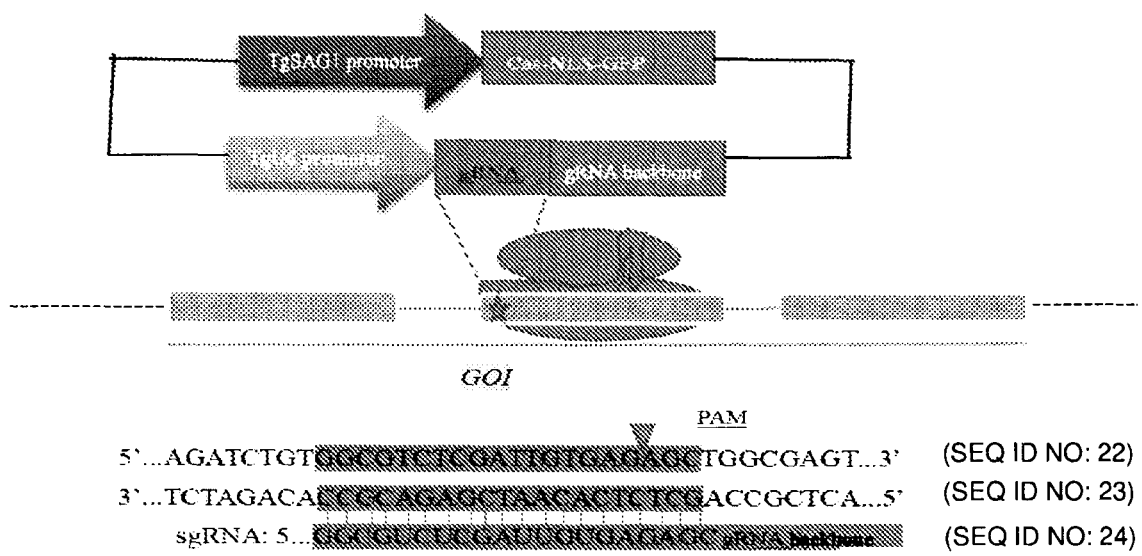
FIG. 2 is a schematic illustration of CRISPR/Cas9 directed homologous gene replacement to knockin EtNMT; a single Cas9-mediated double-stranded break in the target gene is introduced by the plasmid pSAG1-Cas9-U6-sgRNA, where the star is a Cas9 cleavage site of the gene of interest, the *Toxoplasma gondii* SAG1 promoter (TgSAG1) is used to drive expression of the Cas9 protein that include a nuclear localization sequence (NLS) fused to EGFP (Cas9-NLS-EGFP), and the U6 promoter of *T. gondii* is used to drive expression of a single-guide RNA (sgRNA); and the fragments containing target sequences and gRNA sequence for knockin are set forth in SEQ ID NOS: 22-24, respectively, where the underlined sequence in SEQ ID NO: 22 is a protospacer adjacent motif (PAM), the triangle indicate a cleavage site and the shaded areas in SEQ ID NOS: 22-24 are target sequences and gRNA sequence for knockin, respectively.

The present disclosure provides a method for knocking out an NMT gene from *Eimeria tenella*, including: mixing sporozoites of *Eimeria tenella* with a pCRISPR::EtNMT plasmid and a pEtNMT::DHFR plasmid, and subjecting a resulting mixture to electrotransformation to obtain NMT gene-knockout *Eimeria tenella*.

In the present disclosure, the sporozoites of *Eimeria tenella* may be mixed with the pCRISPR::EtNMT plasmid and the pEtNMT::DHFR plasmid at a number-mass-mass ratio preferably of $(0.5$-$1.5 \times 10^7)$ sporozoites:(3-8) μg:(0.5-1.5) μg, and more preferably of $1 \times 10^7$ sporozoites:5 μg:1 μg. In the present disclosure, the sporozoites of *Eimeria tenella* may preferably be resuspended in an electroporation buffer, and then mixed with the pCRISPR::EtNMT plasmid and the pEtNMT::DHFR plasmid. In the present disclosure, the electrotransformation may preferably be conducted under the following conditions: voltage: 2,000 v, capacitance: 25 μF, and two electric shocks under capacitance ∞.

The present disclosure has no specific limitation on a method for obtaining the sporozoites of *Eimeria tenella*, and a conventional method may be adopted. The present disclosure has no specific limitation on a source of *Eimeria tenella*, and a conventional source may be adopted.

In the present disclosure, a construction method of the pCRISPR::EtNMT plasmid may preferably include: with a pSAG1::Cas9-U6::sgUPRT plasmid as a template, conducting amplification using a CRISPR-EtNMT-F primer and a CRISPR-R primer to obtain an amplification product; subjecting the amplification product to KLD reaction to obtain a reaction product; and transforming the reaction product into competent cells, and extracting a resulting plasmid to obtain the pCRISPR::EtNMT plasmid; the CRISPR-EtNMT-F primer may have a nucleotide sequence shown in SEQ ID NO: 1; and the CRISPR-R primer may have a nucleotide sequence shown in SEQ ID NO: 2.

In the present disclosure, a DHFR gene is added to the pSAG1::Cas9-U6::sgUPRT plasmid (Addgene, catalog number: 54467), and the DHFR gene is added between the Amp+ gene and the SAG 5'UTR sequence.

In the present disclosure, the CRISPR-EtNMT-F primer has a nucleotide sequence shown in SEQ ID NO: 1, specifically as follows:
  gctgtgtgtcccagaacagggttttagagctagaaatagc, where, the underlined bases are target sites; and
  the CRISPR-R primer has a nucleotide sequence shown in SEQ ID NO: 2, specifically as follows:
  aacttgacatccccatttac.

The present disclosure may preferably conduct Basic Local Alignment Search Tool (BLAST) using the EAH_00054370 sequence as a template (parameter: database: RefSeq Representative genome (RefSeq_representative_genomes), and select "*Eimeria tenella* (taxid: 5802)" as the organism. The present disclosure finds that the EtNMT gene is located in Eth_Scaff32 in the genome of *Eimeria tenella*, and designs EtNMT-F (SEQ ID NO: 9) and EtNMT-R (SEQ ID NO: 10) after using homologous sequences and related species for prediction.
  SEQ ID NO: 9: 5'-ATGCCTGCAGACTGCAAAGAAAATGCAGC-3'; and
  SEQ ID NO: 10: 5'-TTAGAGGAGCGCCAAGCCAATATCTTTGTGCA-3'.

The EtNMT gene is amplified with EtNMT-F and EtNMT-R by a conventional method.

The present disclosure conducts target sequence prediction based on the EtNMT gene:
  the obtained EtNMT gene sequence is entered into the online website E-CRISP (www.e-crisp.org/E-CRISP/designcrispr.html). to obtain a gene knockout target site; and a target sequence is (SEQ ID NO: 11) CCTGTTCTGGGACACACAGC, which is the (+195) to (+214) bp behind the start codon ATG of the EtNMT gene. The present disclosure designs the EtNMT-F primer and the EtNMT-R primer according to the target sequence.

The present disclosure may preferably use the CRISPR-EtNMT-F primer and CRISPR-R primer for amplification. Every 28.5 µl of a system used for the amplification may preferably include: Q5 hot start high-Fidelity 2× Master Mix: 12.5 µl; CRISPR-EtNMT-F primer: 1.25 µl; CRISPR-R primer: 1.25 µl; pSAG1::Cas9-U6::sgUPRT plasmid: 1 µl; and Nuclease-free water: 12.5 µl. A procedure used for the amplification may preferably include: 98° C. for 30 s, 98° C. for 10 s, 55° C. for 30 s, 72° C. for 2 min, 35 cycles; and 72° C. for 2 min. In the present disclosure, reagents used for the amplification may preferably come from the Q5 site-directed mutagenesis kit (NEB, #E0552S).

In the present disclosure, every 10 µl of a system for the KLD reaction may preferably include: amplification product: 1 µl; 2× KLD reaction buffer: 5 µl; 10× KLD enzyme Mix: 1 µl; and Nuclease-free water: 3 µl. In the present disclosure, the KLD reaction may preferably be conducted at 25° C. to 30° C. for 5 min. The present disclosure has no specific limitation on a source of the reagent, and a conventional commercial reagent may be used.

The present disclosure may preferably transform the reaction product into competent cells and extract a resulting plasmid to obtain the pCRISPR::EtNMT plasmid. The present disclosure has no specific limitation on a type and source of the competent cells, and conventional competent cells may be adopted. The present disclosure has no specific limitation on a method for the transformation, and a conventional transformation method may be adopted. The present disclosure has no specific limitation on a method for the plasmid extraction, and a conventional plasmid extraction method may be adopted.

In the present disclosure, the pCRISPR::EtNMT plasmid is a knockout plasmid.

In the present disclosure, a construction method of the pEtNMT::DHFR plasmid may preferably include: ligating upstream 5'UTR of an EtNMT gene, DHFR-TS*, and downstream 3'UTR of the EtNMT gene into a pcDNA3.1 (+) vector to obtain a ligated vector; transforming the ligated vector into competent cells; and extracting a resulting plasmid to obtain the pEtNMT::DHFR plasmid.

The present disclosure may preferably conduct amplification by a conventional method using EtNMT5'UTR-F and EtNMT5'UTR-R with the *Eimeria tenella* genome as a template to obtain the upstream 5' UTR of the EtNMT gene.

In the present disclosure, the upstream 5' UTR of the EtNMT gene has a nucleotide sequence shown in SEQ ID NO: 18, specifically as follows:

cctaaaccctaatgctaaacccttatgttagcaaacggatggcatcttta taggataaatatgaaatgcatctgaagttgtttggttttccatttcgcac tttgagtgcaaaccctaacccgtaaaccctaaaccctaaaccctaaaccc cgaaccctaaaccctagcctcctagccctgtaacagctctgcgtgtgtt tccgaattcattctttggcacttctttgattttgcaattcaaatcattta taatttcaatttatttcaaatatcttttattttatttattttaaaagaag ttaaaacccgctgcggccgctggctgccgactttggcgaacttgaattt caagtgtctgcacgagttgaactcagaacttgaacgaagaggggaaactg cgcatttctggggctaaaaaggccgaaagagacaaaaataaatgaataaa ttgaataaaagtgcagataaatggagaattcgaggaagatattcacaaaa tcgagatcttttcctcggagtttcttcggatgaggcgttgctgtttccaa aacgaacacagcaactcgcgggcactgcggagccgattcggcgccaaaat taacgcttttagcgtcatctgcgtcaaattgaacggcgaaaccgaatta attacaaaaactaaattaatttgcgcctttaagtgttaaaaacgggccaa gaggcgcaaaagaggggagcagccgtccctgtgctccgacagccccagc tgtacagacagcatgcggcgctggcagtgcgtgtgccggtttaaaattaa attaaattatttattttaataaatttgataaatttaatttgtggattctt tgttttcacccgagcttcgcgcggaaccacctccaacccgcggccccg ctgtctttgatcggatcggacttgttcggggctcttttttctcttcttttt ctctccttttgaattcttcttttccaaaattaattttattttactttaag aacttcaaactctccgggacgcccttgttgctgcttttctcccgaggcc acggacccccagcgccaaaatgcctgcagactgcaaa.

In the present disclosure, the EtNMT5'UTR-F has a nucleotide sequence shown in SEQ ID NO: 12, specifically as follows:
  ctagcgtttaaact-
    taagcttCCTAAACCCTAATGCTAAACCCTT, where, the sequence ctagcgtttaaacttaagctt expressed by small letters is a homologous arm required for ligating multiple fragments, and aagctt is the Hind III enzymatic cleavage site.

In the present disclosure, the EtNMT5'UTR-R has a nucleotide sequence shown in SEQ ID NO: 13, specifically as follows:

gaactacgcgTTTGCAGTCTGCAGGCATTTT, where, the sequence expressed by small letters is a homologous arm required for ligating multiple fragments.

In the present disclosure, ORF of the EtNMT gene has a full-length nucleotide sequence shown in SEQ ID NO: 19, specifically as follows:

atgcctgcagactgcaaagaaaatgcagcagcagcagacgcagcagcaga tccgcagcagcagcagcagcaacagcaagcaacagcagcagcagcagcag caaaaaacccagacagctcgcccaatgccggaggggatgccctcagcggc agctttgactcgagccatgagaggattgtctgtggcccccacctgttct gggacacacagccagtggtgaaggcagcggagcgggcggcgctggcccca caggatgagggccctattgacgctccgaaaacagtagatgatgttagaaa ggagccttacaatttgccaagtggttttatttggtctgaatgttcggtgg aagacccgcaggccttggacgaggtgtactggctgctgagcgaacactac gtggaagacgaagacaatttgtttcgttttaattacagccgggagttttt gttttgggctttgactccccgggggcctttagggagtggattgtgggcg tgcgcgtagcagcaaacaacaaacttgtggggctaattacggcgagccct gctgcagtgagctgcagcagcaaaacgctgcagctggcggaggtgaattt tctgtgtgtgcacaagaagctgcgaagcaaaagactggctcctgtgctta tcaaggaaatcactcggcgggtaaatctcaagggcatttggcaggccgtc tatacagcaggagttgtgctgccgacgccagtggcggagtgccgttattg gcacagatctttaaatcccaaaaagttaattgaagttggatttagcggac ttggaaaaagaatgacaattagccggagtattaagctttatagggtggcg gagtcgccggcgatcgaagggctgagggaaatgaaggccggagacgtttc gaaagttcaaaagttgttgatgaattatttggaacagttcaaacttcacc cagtgttttcggaggaagaaatttctcattggttagttccaagagaagga gttgttcatgtttatgttcgggaagaagaaggagaagtgacggatttaat ttctttttacgaattgccttcttctgtaattggacacagaaaacacaaag aagtcaaagctgcttattcttttacaacgtggccacttcggtgccgctg aaagaacttatgcaagacgcccttgcctcgccaaacaaaaagacttcga cgtatttaacgcgttggatgtaatggaaaataaaaccttcgtggaggaat tgaagtttggagttggcgacgggtttctgcggtattaccttttacaactgg cgctgctctccgttgctgcacaaagatattggcttggtgctcctctaa.

The present disclosure may preferably use the DHFR-F primer and the DHFR-R primer to amplify a DHFR-TS* gene by a conventional method with the pSAG1::Cas9-U6::sgUPRT (pSAG1::Cas9-U6::sgUPRT has the DHFR-TS* gene) plasmid of *Toxoplasma gondii* as a template, and the DHFR-TS* gene has the same nucleotide sequence as that published in the literature (Shen B, Brown KM, Lee TD, Sibley LD. Efficient gene disruption in diverse strains of *Toxoplasma gondii* using CRISPR/CAS9. MBio. 2014; 5 (3): e01114-14.).

In the present disclosure, the DHFR-TS* gene is used as a drug resistance gene: the dihydrofolate reductase (DHFR) of dihydrofolate reductase-thymidylate synthase (DHFR-TS) is a target site of pyrimethamine. Mutations in the DHFR region are correlated with resistance to antifolates. Since DHFR includes two amino acid mutations DHFRm2m3-TS, DHFR is a drug screening marker, and there are mutations at amino acids 65 and 113 in DHFR-TS*. Mutation at 65 (mutation of serine (Ser) to arginine (R)) and mutation at 113 (mutation of tyrosine to aspartic acid) allow a high pyrimethamine-resistance level, so it has been used as a positive selection marker for various transfection vectors. In the present disclosure, homologous recombination is used to insert the pyrimethamine-resistant fragment DHFR at a gene deletion site, and pyrimethamine is used to screen strains integrated with the pyrimethamine-resistant fragment DHFR.

The present disclosure has no specific limitation on a source of the pSAG1::Cas9-U6::sgUPRT, and a conventional commercial product may be used.

In the present disclosure, the DHFR-F primer has a nucleotide sequence shown in SEQ ID NO: 14, specifically as follows:

agactgcaaaCGCGTAGTTCCTGTGTGTCATT, where, the sequence expressed by small letters is a homologous arm required for ligating multiple fragments.

the DHFR-R primer has a nucleotide sequence shown in SEQ ID NO: 15, specifically as follows:

agcaccaagcGGAATTCCATCCTGCAAGTG.

The present disclosure may preferably conduct amplification by a conventional method using the EtNMT3'UTR-F and EtNMT3'UTR-R primers with the *Eimeria tenella* genome as a template to obtain the downstream 3' UTR of the EtNMT gene.

In the present disclosure, the downstream 3' UTR of the EtNMT gene has a nucleotide sequence shown in SEQ ID NO: 21, specifically as follows:

gcttggtgctcctctaaaccctaaaatagggtttagggtttacggcctag ggtttgcttcgcatcttgtcgccgcgctgctgaagcagcagcgctgctgc agcagcagcgctgctgcacatctgcagcagaagcaaggctgctgctgcgg cagcaaaagcagcagcaacagcagcaaagcagcagctgcagcagcaacag cgacgaagcagcagctgcagcagcagcagctgcagcagcaacagcagcag cacaaagcagctgcagcaccgcagaacagcggaggcgcctttgctgcagc agcaacaaggactggcgtgtctatttgtttactactcttattatcattta tttattttattttattttatttatttgtttagatttattgtctcagt tttgcgtccacaaacagaaatccacatttcctggagtcgagaggttgcag cagcagcagcagcgctatctgctgctgctgttgctgctgcaactgctgca ggtgctgctgctgcagcatgaactcagttgcagctaaaacgcagctgcag ctgcaaaaaagaattggggaacaaaaaacaaaagagcagccaagccccta aaccctaaaccctaaaccctccttattccgagaaaaaggagattcgaagg gagctgcttgctgcagcgcatctgatgcagcaactactgcagcaaatact gcagctcgtgcagcaaatgctgcagcaagtgctgcagcaagtgcaagttc tgcagcaagtgctgcagcaagtgccagtgctacagcgagtgctgcagcaa gtgctgcagcaagtgctgcagcaagtgccagtgctacagcgagtgctgca -continued gcaagtgctgcagcaagtgctgcagcaagtgctgcagcaagtgccagtgc tgcagcaagtgctgcagcaagtgctgcagcaagtgctgcagcaagtactg cagcaagtgctgcagcagcacttgctgcagcgtcagagggcgaagaggat ggcgctgagttcctggcggccgcggtgtct In the present disclosure, the EtNMT3'UTR-F primer has a nucleotide sequence shown in SEQ ID NO: 16, specifically as follows:

atggaattccGCTTGGTGCTCCTCTAAACCC; and the EtNMT3'UTR-R primer has a nucleotide sequence shown in SEQ ID NO: 17, specifically as follows:

ccacactggactagtggatccAGACACCGCGGCCGCCAG, where, the sequence expressed by small letters is a homologous arm required for ligating multiple fragments, and ggatcc is the BamH I enzymatic cleavage site.

In the present disclosure, the pcDNA3.1 (+) vector may preferably be first double-digested with Hind III and BamH I and then ligated. The present disclosure has no specific limitation on a method for the double digestion, and a conventional method for double-digesting a vector using the two enzymes may be adopted.

In the present disclosure, every 10 μl of a system for the ligation may preferably include: 5× In-fusion enzyme premixture: 2 μl; DHFR-TS* gene: 1 μl; upstream 5'UTR of EtNMT gene: 1 μl; downstream 3'UTR of EtNMT gene: 4 μl; and pcDNA3.1 (+) vector: 2 μl. In the present disclosure, the ClonExpress MultiS One Step Cloning Kit may preferably be used to ligate the upstream 5'UTR of the EtNMT gene, DHFR-TS*, and the downstream 3'UTR of the EtNMT gene sequentially to the pcDNA3.1 (+) vector. In the present disclosure, the ligation may preferably be conducted at 37° C. for 15 min and then at 50° C. for 15 min. The present disclosure may preferably transform the obtained ligation product into Stbl3 competent cells. The present disclosure has no specific limitation on a method for the transformation, and a conventional transformation method may be adopted. The present disclosure has no specific limitation on a method for the plasmid extraction, and a conventional plasmid extraction method may be adopted.

In the present disclosure, the pEtNMT::DHFR plasmid is a targeting plasmid, which is used as a drug screening plasmid. The DHFR-TS* gene is used to replace the EtNMT gene in the genome for screening pyrimethamine-resistant strains. An obtained strain is a strain in which the DHFR gene is integrated into the genome.

In the present disclosure, after the electrotransformation, the method further includes: inoculating an obtained electrotransformation product into MDBK cells for cultivation, adding pyrimethamine at 6 h, and collecting host cells at 24 h; lysing and digesting the host cells to obtain cells with sporozoites, attacking chicks using the cells with sporozoites, and collecting feces to obtain oocysts; cultivating the oocysts into adult *Eimeria tenella*, and extracting genomic DNA (gDNA) of the adult *Eimeria tenella*; and with the gDNA as a template, conducting amplification using a PCR1 primer pair, a PCR2 primer pair, and a PCR3 primer pair, separately, where, when fragments can be obtained from both the amplification using the PCR1 primer pair and the amplification using the PCR2 primer pair, but no fragments can be obtained from the amplification using the PCR3 primer pair, the *Eimeria tenella* is NMT gene-knockout *Eimeria tenella*.

The present disclosure may preferably inoculate an obtained electrotransformation product into MDBK cells for cultivation, add pyrimethamine at 6 h, and collect host cells at 18 h.

In the present disclosure, the MDBK cells may preferably be cultivated in a cell flask, and after 80% of the bottom of the cell flask is covered with a monolayer of cells, the electrotransformation product is inoculated at an inoculation density preferably of $1 \times 10^7$ sporozoites. In the present disclosure, the cell flask may preferably include DMEM medium with 100 mL/L fetal bovine serum (FBS), 2 mmol/L glutamine, 200 U/mL penicillin, and 20 mg/L streptomycin, and the electrotransformation product is cultivated in the DMEM medium. The cultivation may preferably be conducted in an incubator at a temperature preferably of 41° C. and a $CO_2$ concentration preferably of 50 ml/L. At 6 h of the cultivation, pyrimethamine is added to the culture flask at a final concentration preferably of 150 ppm. The role of adding pyrimethamine is as follows: DHFR of DHFR-TS is a target site for pyrimethamine, and DHFR includes 2 amino acid mutations DHFRm2m3-TS, which allows a high pyrimethamine-resistance level, so the strains surviving at high concentrations of pyrimethamine are strains integrated with the genome editing of DHFR-TS*. At 24 h, host cells are collected.

The present disclosure may preferably lyse and digest the host cells to obtain cells with sporozoites, attack chicks using the cells with sporozoites, and collect feces to obtain oocysts. The present disclosure has no specific limitation on a method for the lysis and digestion, and a conventional method may be adopted. The lysis and digestion allows the release of parasites, and then collected cells with sporozoites from digestion are used to attack chicks via *cloacae*. The chicks may preferably have an age of 3 days. The present disclosure may preferably collect feces on days 6 to 9 of attacking the chicks. After the oocysts are harvested, the chicks are attacked again; pyrimethamine is added to the drinking water or feed for the chicks at a final concentration preferably of 150 ppm; feces is collected on days 6 to 9 to obtain oocysts; and the above steps are repeated once to obtain oocysts screened by pyrimethamine 3 times.

The present disclosure may preferably cultivate the oocysts obtained from 3 times of screening into adult *Eimeria tenella*, and extract gDNA of the adult *Eimeria tenella*, and conduct amplification using a PCR1 primer pair, a PCR2 primer pair, and a PCR3 primer pair separately with the gDNA as a template. When fragments can be obtained from both the amplification using the PCR1 primer pair and the amplification using the PCR2 primer pair, but no fragments can be obtained from the amplification using the PCR3 primer pair, the *Eimeria tenella* is NMT gene-knockout *Eimeria tenella*.

The present disclosure has no specific limitation on a method for extracting the gDNA of *Eimeria tenella*, and a conventional method may be adopted.

The present disclosure preferably may use a PCR1 primer pair, a PCR2 primer pair, and a PCR3 primer pair separately to conduct amplification, with the gDNA as a template. The present disclosure has no specific limitation on a system and procedure used for the amplification, and a conventional system and procedure may be used.

In the present disclosure, the PCR1 primer pair includes PCR1-F and PCR1-R, the PCR1-F has a nucleotide sequence shown in SEQ ID NO: 3, specifically as follows: gatcggatcggacttgttcggggctcttt, and the PCR1-R has a nucleotide sequence shown in SEQ ID NO: 4, specifically as follows: gctgcgggccattgcggtgtcgtggatt.

In the present disclosure, the PCR2 primer pair includes PCR2-F and PCR2-R, the PCR2-F has a nucleotide sequence shown in SEQ ID NO: 5, specifically as follows: atgtgcgtgtatccactcgtgaatgcgttat, and the PCR2-R has a nucleotide sequence shown in SEQ ID NO: 6, specifically as follows: acaagatgcgaagcaaaccctaggccgtaa.

In the present disclosure, the PCR3 primer pair includes PCR3-F and PCR3-R, the PCR3-F has a nucleotide sequence shown in SEQ ID NO: 7, specifically as follows: aatttctcattggttagttccaagagaag, and the PCR3-R has a nucleotide sequence shown in SEQ ID NO: 8, specifically as follows: cccgtcgccaactccaaacttcaattc.

The technical solutions provided by the present disclosure will be described in detail below with reference to examples, but the examples should not be construed as limiting the claimed scope of the present disclosure.

Example 1

Preparation of Sporozoites of *Eimeria tenella* (Guangdong Strain)

An *Eimeria tenella* strain stored in a 2.5% potassium dichromate solution (from a conventional source) was adopted, and centrifugation was conducted at 3,600 rpm for 5 min to remove the potassium dichromate solution. Obtained *Eimeria tenella* was resuspended with PBS (0.01 M, pH 7.4), and a resulting suspension was centrifuged at 3,600 rpm for 5 min; and the above operations were repeated three times. Then an obtained precipitate was resuspended with saturated brine (at room temperature, the solubility of NaCl in water: 36.0 g of NaCl can be dissolved in 100 g of water), and a resulting suspension was centrifuged at 2,000 rpm for 10 min to obtain a supernatant; then water was added to the supernatant (a volume ratio of supernatant to water: 1:5), and a resulting solution was centrifuged at 3,600 rpm for 10 min to obtain purified oocysts. The oocysts were resuspended with PBS (0.01 M, pH 7.4), then added with 200 mm glass beads (a ratio of PBS to glass beads: 1:1), and beaten with wrist force until 95% of sporulated oocysts underwent excystation; and Hanks solution or PBS (0.01 M, pH 7.4) was used to prepare a digestion solution including 0.25% trypsin and 0.75% deoxycholate. The digestion solution was added to the sporocyst suspension, and a resulting solution was incubated in a shaker at 41° C.; the digestion was terminated when many sporozoites were released; a resulting solution was centrifuged at 3,600 rpm for 10 min to obtain a precipitate; the precipitate was then washed with PBS (0.01 M, pH 7.4) and a resulting suspension was centrifuged at 3,600 rpm for 10 min, and the above washing process was conducted three times; an obtained precipitate was resuspended with PBS (0.01 M, pH 7.4) to obtain a sporozoite suspension; and the sporozoite suspension was subjected to suction filtration with a G3 funnel and then centrifuged at 3,600 rpm for 10 min to obtain a precipitate, namely, purified sporozoites.

Example 2

Construction of the Knockout Plasmid pCRISPR::EtNMT and the Homologous Template Plasmid pEtNMT::DHFR for Drug Screening (1) Cloning of the EtNMT Gene of *Eimeria tenella* (Guangdong Strain):

Total RNA was extracted from the oocyst of *Eimeria tenella*, and cDNA synthesis was conducted using one-step RT-PCR kit (Takara Bio, Japan). The keyword "glycylpetide N-tetradecanoyltransferase" was entered on the online website ToxoDB (toxodb.org/toxo/). There was glycylpetide N-tetradecanoyltransferase of *Eimeria acervulina* related to the species in the ToxoDB database, with ToxoDB No: EAH_00054370, but there was no *Eimeria tenella*. Therefore, Basic Local Alignment Search Tool (BLAST) was conducted using the EAH_00054370 sequence as a template (parameter: database: RefSeq Representative genome (RefSeq_representative_genomes), and "*Eimeria tenella* (taxid: 5802)" was selected as the organism. The EtNMT gene was located in Eth_Scaff32 in the genome of *Eimeria tenella*, and EtNMT-F (SEQ ID NO: 9: 5'-atgcctgca-gactgcaaagaaaatgcagc-3') and EtNMT-R (SEQ ID NO: 10: 5'-ttagaggagcgccaagccaatatctttgtgca-3') were designed after prediction was conducted using homologous sequences and related species, so as to amplify the EtNMT gene.

(2) Target Sequence Prediction was Conducted for the EtNMT Gene of *Eimeria tenella* (Guangdong Strain):

the obtained EtNMT gene sequence of *Eimeria tenella* (Guangdong strain) was entered into the online website E-CRISP (NMT) to obtain a gene knockout target site; and a target sequence (SEQ ID NO: 11) was cctgttctgggacacacagc, which was the (+195) to (+214) bp behind the start codon ATG of Etnmt. Designed primers were as follows:

CRISPR-EtNMT-F (SEQ ID NO: 1) (NMT target-specific gRNA sequence) (GCTGTGTGTCCCAGAACAGGGTTT-TAGAGCTAGAAATAGC) and CRISPR-R (GOI-gRNA-Rv) (SEQ ID NO: 2) (AACTTGACATCCC-CATITAC).

(3) Construction of the pCRISPR::EtNMT Plasmid:

The above CRISPR-EtNMT-F and CRISPR-R were used as primers, the pSAG1::Cas9-U6::sgUPRT plasmid was used as a template, and the Q5 site-directed mutagenesis kit (NEB, #E0552S) was used.

TABLE 1

| Amplification system | |
|---|---|
| Q5 hot start high-Fidelity 2x Master Mix | 12.5 μL |
| 10 μmol/L CRISPR-EtNMT-F primer | 1.25 μL |
| 10 μmol/L CRISPR-R primer | 1.25 μL |
| pSAG1::Cas9-U6::sgUPRT plasmid template | 1 μL |
| Nuclease-free water | 12.5 μL |

Cycle conditions were set as follows:

98° C. for 30 s, 98° C. for 10 s, 55° C. for 30 s, 72° C. for 2 min, 35 cycles; and 72° C. for 2 min.

Then, the obtained PCR product was subjected to KLD reaction, and a reaction system was shown in Table 2:

TABLE 2

KLD reaction system at room temperature

| | |
|---|---|
| PCR product | 1 μL |
| 2× KLD reaction buffer | 5 μL |
| 10× KLD enzyme Mix | 1 μL |
| Nuclease-free water | 3 μL |

The KLD enzyme mixture includes mixed kinase, ligase and DpnI enzyme, and also includes a buffer in which all enzymes remain active. In this system, effective phosphorylation and intramolecular ligation/cyclization can be conducted, and the reaction is conducted at room temperature for 5 min to achieve transformation of competent cells.

Then 5 μL of the KLD mixture was added to competent cells for transformation, the CRISPR-EtNMT-F and CRISPR-R were used for identification, and sequencing was conducted. An obtained EtNMT-specific gRNA sequence was used to replace the target sequence of the template plasmid to obtain the pCRISPR::EtNMT plasmid.

(a) Construction of the Knockout Plasmid

Target prediction was conducted for the EtNMT gene sequence of *Eimeria tenella*. Primers CRISPR-EtNMT-F (GOI-gRNA-Fw) and CRISPR-R(GOI-gRNA-Rv) were designed according to the predicted target sequence (see Table 1). The knockout target of EtNMT gene of *Eimeria tenella* (Guangdong strain) had a sequence of CCTGTTCTGGGACACACAGC, which was the (+195) to (+214) bp behind the start codon ATG of EtNMT. This sequence was used to replace the UPRT target sequence in the pSAG1::Cas9-U6::sgUPRT vector, and with the pSAG1::CAS9-U6::sgUPRT as a template, the Q5 site-directed mutagenesis kit (NEB, #E0552S) was used to replace the target sequence in the template plasmid with the NMT target-specific gRNA sequence to obtain the pCRISPR::EtNMT plasmid.

A sequencing result showed that a primer sequence had been integrated into the plasmid as shown in SEQ ID NO: 20 in which the bold sequence represents the primer sequence. The specific sequence is as follows:

gagcgcagcgagtcagtgagcgaggaagcggaagagcgcccaatacgcaa accgcctctccccgcgcgttggccgattcattaatgcagctggcacgaca ggtttcccgactggaaagcgggcagtgagcgcaacgcaattaatgtgagt tagctcactcattaggcacccaggctttacactttatgcttccggctcg tatgttgtgtggaattgtgagcggataacaatttcacacaggaaacagct atgaccatgattacgccaagctcgaaattaaccctcactaaagggaacaa aagctggagctcaaaaaagcaccgactcggtgccacttttcaagttgata acggactagccttattttaacttgctatttctagctctaaaaccctgttc tgggacacacagcaacttgacatccccatttaccagaaggcaaacacccc cttcggggacgaggtgaccctgcgcgacagaaagcccccttcgaagagcgc acagggaggaagcaggcctctgcaggtcgccatttgaaaatctgacagaa ctgatggaaatatgattcttgtcagagaagacattcgagagttcgaaggt ttcccccttggctctacatatcccagtgtctcgcgttctgcaggaggcgc gtcaggcctaggatgcaatattggcgcccaattcacagtgcagcggcgca gccgtcgcaacacttcgcagc.

The sequencing result showed that a suitable pSAG:: Cas9-U6::sgUPRT::NMT gene knockout plasmid was obtained.

(b) Construction of the Homologous Template Plasmid:

(1) Amplification of the upstream fragment of the EtNMT gene: primers EtNMT5'UTR-F and EtNMT5'UTR-R were designed, where the EtNMT5'UTR-F had a Hind III enzymatic cleavage site; and the *Eimeria tenella* genome was used as a template to amplify the upstream 5'UTR fragment

TABLE 3

Target sequence primers used for constructing pCRISPR::EtNMT and primers for the pEtNMT::DHFR plasmid

| Name of primer | 5'-3' | No. | Enzymatic cleavage site |
|---|---|---|---|
| CRISPR-EtNMT-F (GOI-gRNA-Fw) | GCTGTGTGTCCCAGAACAGGGTTTTAGAGCTAGAAATAGC | SEQ ID NO: 1 | None |
| CRISPR-R(GOI-gRNA-Rv) | AACTTGACATCCCCATTTAC | SEQ ID NO: 2 | None |
| EtNMT5'UTR-F | ctagcgtttaaacttaagcttCCTAAACCCTAATGCTAAACCCTT | SEQ ID NO: 12 | Hind III |
| EtNMT5'UTR-R | gaactacgcgTTTGCAGTCTGCAGGCATTTT | SEQ ID NO: 13 | None |
| DHFR-F | agactgcaaaCGCGTAGTTCCTGTGTGTCATT | SEQ ID NO: 14 | None |
| DHFR-R | agcaccaagcGGAATTCCATCCTGCAAGTGC | SEQ ID NO: 15 | None |
| EtNMT3'UTR-F | atggaattccGCTTGGTGCTCCTCTAAACCC | SEQ ID NO: 16 | None |
| EtNMT3'UTR-R | ccacactggactagtggatccAGACACCGCGGCCGCCAG | SEQ ID NO: 17 | BamH I |

Notes:
The underlined sequence is an EtNMT gene knockout target; the sequence expressed by small letters is a homologous arm required for ligating multiple fragments; and the underlined sequence expressed by small letters is the enzymatic cleavage site.

of the EtNMT gene, which was of 1.0 kb and used as an upstream homologous arm sequence.

(2) Amplification of the drug resistance DHFR gene: primers DHFR-F and DHFR-R were designed, and the pSAG1::Cas9-U6::sgUPRT (pSAG1::Cas9-U6::sgUPRT had DHFR-TS*) plasmid of *Toxoplasma gondii* was used as a template to amplify the DHFR-TS* gene.

(3) Amplification of the downstream fragment of the EtNMT gene: primers EtNMT3'UTR-F and EtNMT3'UTR-R were designed, where, there was a BamH I enzymatic cleavage site downstream; and the *Eimeria tenella* genome was used as a template to amplify the downstream 3'UTR fragment of the EtNMT gene, which was of 1.0 kb and was used as a downstream homologous arm.

(4) Enzyme digestion of the ligated vector: the pcDNA3.1 (+) vector was digested with Hind III and BamH I for ligation in the next step.

(5) Ligation for the homologous template plasmid: ClonExpress MultiS One Step Cloning Kit was used to ligate the amplified upstream fragment of the EtNMT gene, the drug resistant DHFR gene fragment, the downstream fragment of the EtNMT gene, and the pcDNA3.1 (+) vector digested with Hind III and BamH I sequentially.

TABLE 4

| Ligation system | |
|---|---|
| 5× In-fusion enzyme premixture | 2 μL |
| DHFR-TS* gene | 1 μL |
| EtNMT5'UTR | 1 μL |
| EtNMT3'UTR | 4 μL |
| pcDNA3.1 (+) plasmid | 2 μL |

Then the reaction system was incubated at 37° C. for 15 min and then at 50° C. for 15 min, and placed on ice; the system was used for transforming Stbl3 competent cells; and positively screening, identification and sequencing were conducted to obtain the successfully-targeting DHFR-resistant plasmid pEtNMT::DHFR.

In *Eimeria tenella*, CRISPR/Cas9-mediated gene destruction and deletion was used, and CRISPR/Cas9-mediated homologous recombination and drug screening gene DHFR-TS* were used to replace the NMT strategy to knock out the EtNMT gene. Therefore, a homologous recombination plasmid was required. The present disclosure used CRISPR/Cas9-mediated site-specific integration to insert a resistance screening element, and generally ligated the upstream homologous arm of the target gene to be deleted with the resistance screening element and the downstream homologous arm of the target gene to be deleted, so as to construct a plasmid as a targeting plasmid. According to the position of the EtNMT gene in the *Eimeria tenella* genome, 1.0 kb before and after the position was selected as homologous arms, and corresponding primers EtNMT5'UTR-F, EtNMT5'UTR-R, EtNMT3'UTR-F, and EtNMT3'UTR-R were used for amplification.

Figure 4:
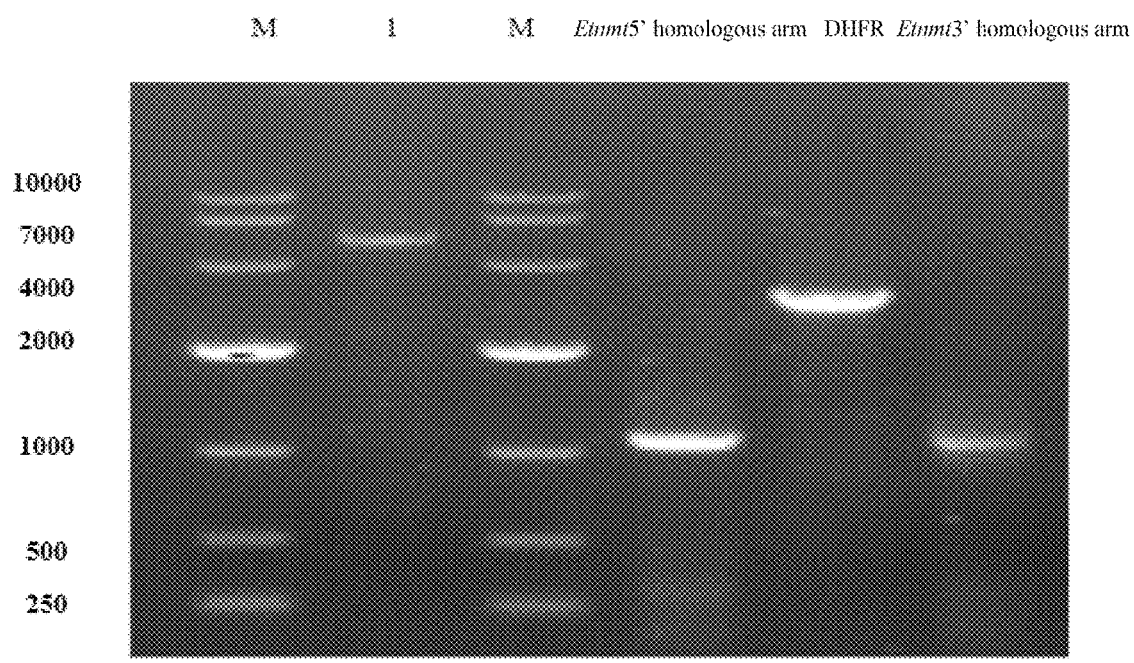
FIG. 4 shows the specific PCR identification of the pEtNMT::DHFR homologous template and the identification of DNA elements required for knocking out EtNMT, where, M: DL10000 marker; 1: specific PCR identification of the pEtNMT::DHFR homologous template (a pEtNMT::DHFR fragment has a size of 5195 bp); and construction of homologous arm: bands with corresponding sizes are obtained for EtNMT5' homologous arm, DHFR, EtNMT3' homologous arm fragments.

In addition, the specific primers DHFR-F and DHFR-R were used to amplify the DHFS-TS* gene (pSAG1::Cas9-U6::sgUPRT had DHFR-TS*, and pSAG1::Cas9-U6::sgUPRT was directly used as a template for amplifying DHFS-TS*). ClonExpress MultiS One Step Cloning Kit (Vazyme, #C113-01/02) was used to ligate the 5' homologous arm, DHFS-TS*, and the 3' homologous arm sequentially and then ligate a resulting product to the pcDNA3.1 (+) vector double-digested with Hind III and BamH I to obtain the pEtNMT::DHFR plasmid. Specific PCR identification was conducted for the plasmid (FIG. 4), which proved successful construction of the plasmid in combination with sequencing analysis.

Figure 3:
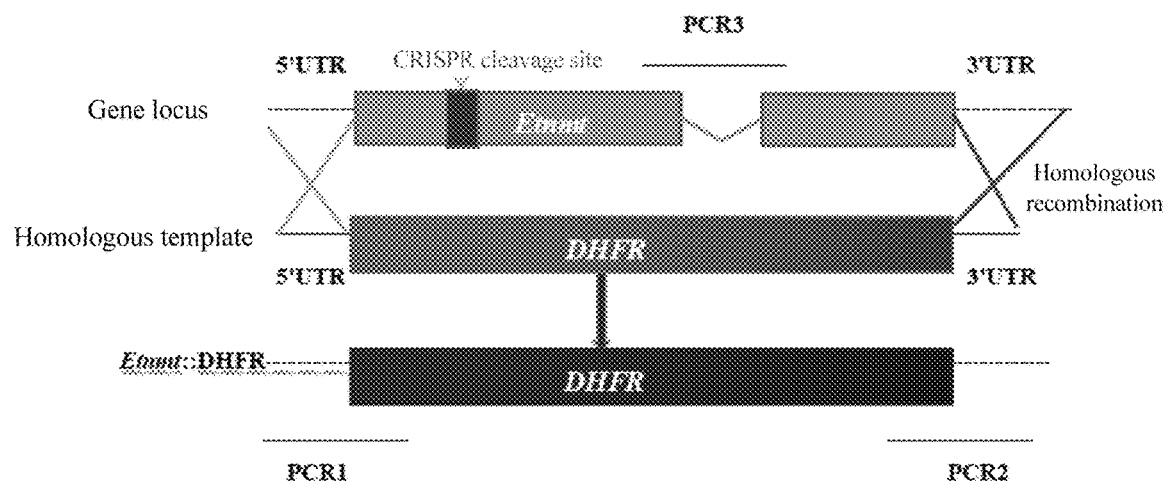
FIG. 3 is a schematic diagram of knocking out the EtNMT gene from *Eimeria tenella* with the CRISPR-Cas9 system.

In *Eimeria tenella*, CRISPR/Cas9-mediated gene destruction and deletion was used. As shown in FIG. 3, CRISPR/Cas9-mediated site-specific integration was used to insert a resistance screening element, and the upstream homologous arm of the EtNMT gene to be knocked out was ligated to the resistance screening element and the downstream homologous arm of the EtNMT gene to be deleted, so as to construct a recombinant plasmid as a targeting plasmid. The pEtNMT::DHFR and pCRISPR::EtNMT plasmids were used to co-transfect the target genome, the pCRISPR::EtNMT was used to cleave the genome, and the pEtNMT::DHFR was integrated into the genome.

The upstream and downstream homologous arms in the present disclosure were of 1.0 kb. The part indicated by an arrow in the EtNMT locus was a targeting site of CRISPR/Cas9, and PCR1-F, PCR1-R, PCR2-F, PCR2-R, PCR3-F, and PCR3-R were PCR primers used for identifying knockout strains.

Example 3

Transfection of *Eimeria tenella* Sporozoites and Screening of Positive Clones

A sporozoite suspension with $1\times10^7$ fresh and vigorous *Eimeria tenella* sporozoites just extracted was taken and added to an electroporation cuvette; the *Eimeria tenella* was resuspended with an electroporation buffer Cytomix (composition of Cytomix: 120 mmol/L KCl, 0.15 mmol/L $CaCl_2$, 10 mmol/L $K_2HPO_4$ with pH 7.6, 25 mmol/L HEPES with pH 7.6, 2 mmol/L EGTA, and 5 mmol/L $MgCl_2$), and then the pCRISPR::EtNMT plasmid (5 μg) and the pEtNMT::DHFR homologous template plasmid (1 lag) were added; a resulting solution was diluted to 800 μL and thoroughly mixed; the electroporation cuvette was placed in the Bio-Rad electroporator, and electric shock was conducted twice under the conditions: voltage: 2,000 v, capacitance: 25 μF, and capacitance: ∞; after the electrotransfection, the sporozoites were inoculated at a density of $1\times10^7$ sporozoites/flask into a culture flask in which 80% of the flask bottom was covered with a monolayer of MDBK cells (before inoculation, the cells were washed twice with 0.1 mol/L PBS at pH 7.2); the cells were cultivated in an incubator at 41° C. and 50 mL/L $CO_2$ using DMEM medium with 100 mL/L FBS, 2 mmol/L glutamine, 200 U/mL penicillin, and 20 mg/L streptomycin; pyrimethamine was added at 6 h of the cultivation (at a final concentration of 150 ppm), and the cells were further cultivated for 18 h; the host cells were lysed and digested to release the *Eimeria tenella*; and then collected cells with sporozoites obtained from the digestion were used to attack 3-day-old chicks via *cloacae*, feces was collected on days 6 to 9 to obtain oocysts, and the oocysts were sporulated; then sporulated oocysts of *Eimeria tenella* were re-inoculated into the chicks, and pyrimethamine was added (at a final concentration of 150 ppm) to the drinking water or feed; feces was collected on days 6 to 9; purified oocysts were obtained by rinsing with saturated brine; and the drugs were screened for 3 generations.

Identification of EtNMT-Deleted Strains (1) The genome was extracted from the *Eimeria tenella* obtained from the 3 generation drug screening in the previous step.

(2) The genome obtained in the previous step was used as a template, and primers PCR1-F (located in the 5'UTR of EtNMT), PCR1-R (located in the upstream of the DHFR gene), PCR2-F (located in the downstream of the DHFR gene), PCR2-R (located in the 3'UTR of EtNMT), PCR3-F (located inside the knockout gene EtNMT), and PCR3-R (located inside the knockout gene EtNMT) (see Table 5 for primer sequences) were designed for PCR. In the present disclosure, the integration of the 5'UTR sequence of the EtNMT gene with the DHFR gene was detected by PCR1; the integration of the 3'UTR sequence of the EtNMT gene with the DHFR gene was detected by PCR2; and whether EtNMT was knocked out was detected by PCR3. If PCR1 and PCR2 are positive and obtained fragments have sizes of 341 bp and 190 bp, respectively, it confirms the integration of the 5'UTR sequence of the EtNMT gene with the DHFR gene and the integration of the 3'UTR sequence of EtNMT with the DHFR gene, indicating that the resistance gene DHFR replaces the EtNMT gene; and if PCR3 is negative, it confirms that there is no EtNMT gene in the genome. In addition, in combination with the sequencing result that an integrated sequence fragment consistent with the theory is obtained, it confirms that EtNMT-knockout *Eimeria tenella* is obtained.

(3) In this example, PCR1 and PCR2 were both positive, PCR3 was negative, and the sequencing result was correct, confirming that a positive EtNMT-knockout *Eimeria tenella* strain was obtained.

TABLE 5

PCR primers used for identifying EtNMT-knockout strains

| Name of primer | Sequence (5'-3') | No. |
|---|---|---|
| PCR1-F | GATCGGATCGGACTTGTTCGGGGCTCTTT | SEQ ID NO: 3 |
| PCR1-R | GCTGCGGGCCATTGCGGTGTCGTGGATT | SEQ ID NO: 4 |
| PCR2-F | ATGTGCGTGTATCCACTCGTGAATGCGTTAT | SEQ ID NO: 5 |
| PCR2-R | ACAAGATGCGAAGCAAACCCTAGGCCGTAA | SEQ ID NO: 6 |
| PCR3-F | AATTTCTCATTGGTTAGTTCCAAGAGAAG | SEQ ID NO: 7 |
| PCR3-R | CCCGTCGCCAACTCCAAACTTCAATTC | SEQ ID NO: 8 |

In this example, the electroporation method was used to co-transfect the homologous fragments of pCRISPR::EtNMT and pEtNMT::DHFR into sporozoites of *Eimeria tenella* (Guangdong strain). After 3 generation screening using pyrimethamine, oocysts were obtained. The oocysts obtained from the screening were subjected to gDNA extraction, and PCR amplification was conducted with different identification PCR primers to identify whether a positive gene knockout *Eimeria tenella* strain was obtained.

Figure 5:
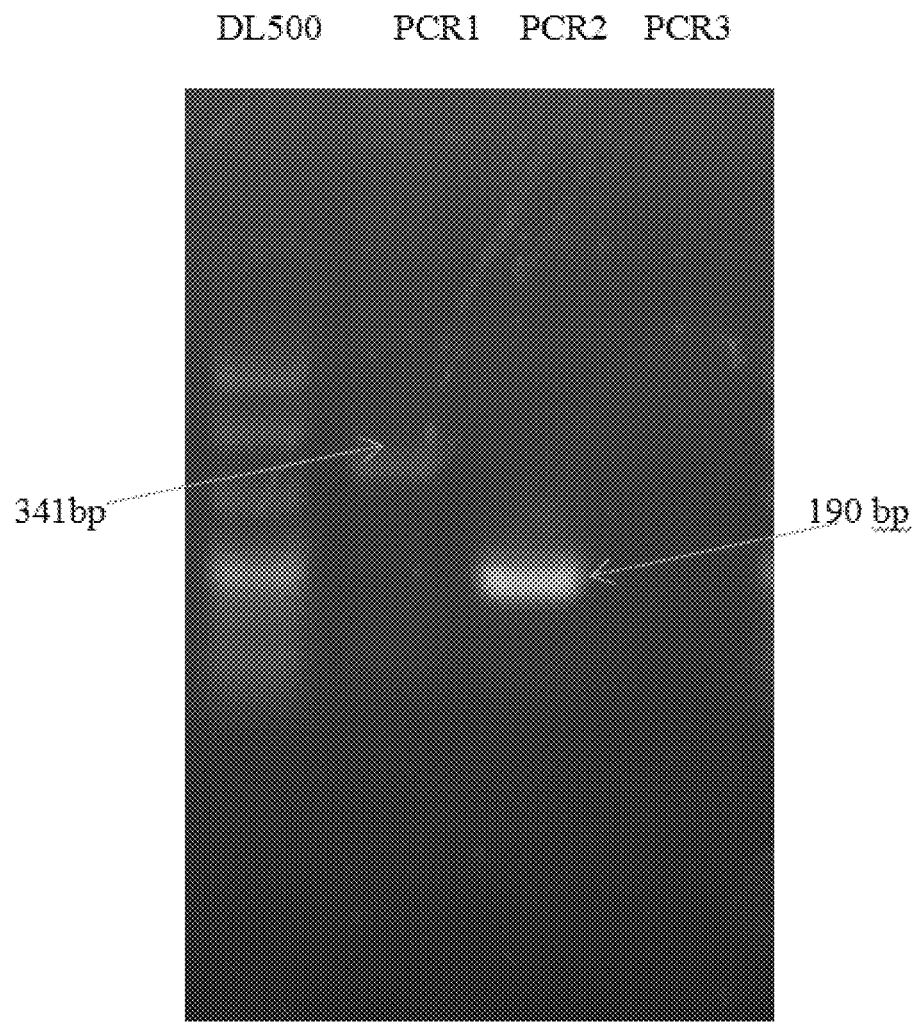
FIG. 5 shows the identification of the EtNMT gene-knockout strain of *Eimeria tenella* (Guangdong strain), where, lane 1 is for DL500 Marker; lane 2 is for a PCR1 product (a fusion fragment of the 5'UTR fragment of EtNMT and a partial DHFR gene), in the genome of the knockout strain, the fusion fragment is integrated into the genome, and the PCR1 product is a 341 bp band; lane 3 is for a PCR2 product (a fusion fragment of a partial DHFR gene fragment and the 3'UTR fragment of EtNMT), in the genome of the knockout strain, this fusion fragment is integrated into the genome, and the PCR2 fragment band has a size of 190 bp; and lane 4 is for a PCR3 product, namely, an internal fragment of the EtNMT gene, which does not exist in the genome of the knockout strain, and no band appears for the PCR product.

Through PCR detection, it was found that the EtNMT gene of all obtained *Eimeria tenella* oocysts was destroyed (PCR3 was negative, PCR1 and PCR2 were both positive) (FIG. 5), indicating that the obtained oocysts were EtNMT gene-deficient *Eimeria tenella* oocysts. These results showed that the EtNMT gene was successively knocked out from *Eimeria tenella* (Guangdong strain).

The present disclosure uses the CRISPR/Cas9 technology for the first time to knock out the NMT gene from *Eimeria tenella*, where, a target of the NMT gene is designed, sgRNA and Cas9 mRNA are synthesized and transcribed, a knockout plasmid and a homologous arm template plasmid are constructed, and then electrotransformation, cell cultivation, drug screening and chick passage are conducted to obtain *Eimeria tenella* oocysts for identification, so as to obtain NMT gene-knockout oocysts of *Eimeria tenella*.

The present disclosure successfully constructs an NMT gene-knockout *Eimeria tenella* strain (Guangdong strain) ΔEtNMT through the CRISPR/Cas9 system, and uses the CRISPR/Cas9 system with the promoters TgU6 and TgSAG1 of *Toxoplasma gondii* for the first time in the study of gene knockout of coccidia, which lays a foundation for studying the biological function of coccidial EtNMT.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for knocking out an N-myristoyltransferase (NMT) gene from *Eimeria tenella*, comprising:
   a. mixing sporozoites of *Eimeria tenella* with a pCRISPR::EtNMT plasmid and a pEtNMT::DHFR plasmid to obtain a sporozoites-plasmids mixture, and
   b. subjecting the sporozoites-plasmids mixture to electrotransformation to obtain NMT gene-knockout *Eimeria tenella*.

2. The knockout method according to claim 1, wherein, 0.5-1.5×10⁷ sporozoites of *Eimeria tenella* are mixed with 3-8 μg of the pCRISPR::EtNMT plasmid and 0.5-1.5 μg of the pEtNMT::DHFR plasmid.

3. The knockout method according to claim 2, further comprising constructing the pEtNMT::DHFR plasmid before step a, comprising:
   i. with a pSAG1::Cas9-U6::sgUPRT plasmid as a template, conducting amplification using a CRISPR-EtNMT-F primer and a CRISPR-R primer to obtain an amplification product;
   ii. subjecting the amplification product to KLD reaction to obtain a reaction product;
   iii. transforming the reaction product into competent cells; and
   iv. extracting a resulting plasmid to obtain the pCRISPR::EtNMT plasmid; wherein
      the CRISPR-EtNMT-F primer has the nucleotide sequence shown in SEQ ID NO: 1; and
      the CRISPR-R primer has the nucleotide sequence shown in SEQ ID NO: 2.

4. The knockout method according to claim 3, wherein, a procedure used for the amplification comprises:
   i. 98° C. for 30 s;
   ii. 98° C. for 10 s, 55° C. for 30 s, 72° C. for 2 min, 35 cycles; and
   iii. 72° C. for 2 min.

5. The knockout method according to claim 2, further comprising constructing the pEtNMT::DHFR plasmid before step a, comprising:
   i. ligating upstream of a 5'UTR of an EtNMT gene, DHFR-TS*, and downstream of a 3'UTR of the EtNMT gene into a pcDNA3.1 (+) vector to obtain a ligated vector;
   ii. transforming the ligated vector into competent cells; and
   iii. extracting a resulting plasmid to obtain the pEtNMT::DHFR plasmid.

6. The knockout method according to claim 1, further comprising constructing the pCRISPR::EtNMT plasmid before step a, comprising:
   i. with a pSAG1::Cas9-U6::sgUPRT plasmid as a template, conducting amplification using a CRISPR-EtNMT-F primer and a CRISPR-R primer to obtain an amplification product; and
   ii. subjecting the amplification product to a Kinase, Ligase, and Don1 (KLD) reaction to obtain a reaction product; and
   iii. transforming the reaction product into competent cells; and
   iv. extracting a resulting plasmid to obtain the pCRISPR::EtNMT plasmid; wherein the CRISPR-EtNMT-F primer has the nucleotide sequence shown in SEQ ID NO: 1; and
   the CRISPR-R primer has the nucleotide sequence shown in SEQ ID NO: 2.

7. The knockout method according to claim 6, wherein, a procedure used for the amplification comprises:
   i. 98° C. for 30 s;
   ii. 98° C. for 10 s, 55° C. for 30 s, 72° C. for 2 min, 35 cycles; and
   iii. 72° C. for 2 min.

8. The knockout method according to claim 1, further comprising constructing the pEtNMT::DHFR plasmid before step a, comprising:
   i. ligating upstream of a 5'UTR of an EtNMT gene, DHFR-TS*, and downstream of a 3'UTR of the EtNMT gene into a pcDNA3.1 (+) vector to obtain a ligated vector;
   ii. transforming the ligated vector into competent cells; and
   iii. extracting a resulting plasmid to obtain the pEtNMT::DHFR plasmid.

9. The knockout method according to claim 1, wherein, after the electrotransformation, the method further comprises:
   i. inoculating an obtained electrotransformation product into MDBK cells for cultivation, adding pyrimethamine at 6 h, and collecting host cells at 18 h;
   ii. lysing and digesting the host cells to obtain cells with sporozoites;
   iii. attacking chicks using the cells with sporozoites;
   iv. collecting feces to obtain oocysts;
   v. cultivating the oocysts into adult *Eimeria tenella*;
   vi. extracting genomic DNA (gDNA) of the adult *Eimeria tenella*; and
   vii. with the gDNA as a template, conducting amplification using a PCR1 primer pair, a PCR2 primer pair, and a PCR3 primer pair, separately, wherein, when fragments can be obtained from both the amplification using the PCR1 primer pair and the amplification using the PCR2 primer pair, but no fragments can be obtained from the amplification using the PCR3 primer pair, the *Eimeria tenella* is NMT gene-knockout *Eimeria tenella*.

10. The knockout method according to claim 9, wherein,
a) the PCR1 primer pair comprises PCR1-F and PCR1-R, the PCR1-F has the nucleotide sequence shown in SEQ ID NO: 3, and the PCR1-R has the nucleotide sequence shown in SEQ ID NO: 4;
b) the PCR2 primer pair comprises PCR2-F and PCR2-R, the PCR2-F has the nucleotide sequence shown in SEQ ID NO: 5, and the PCR2-R has the nucleotide sequence shown in SEQ ID NO: 6; and
c) the PCR3 primer pair comprises PCR3-F and PCR3-R, the PCR3-F has the nucleotide sequence shown in SEQ ID NO: 7, and the PCR3-R has the nucleotide sequence shown in SEQ ID NO: 8.

* * * * *